United States Patent [19]
Bernoux et al.

[11] Patent Number: 5,329,357
[45] Date of Patent: Jul. 12, 1994

[54] SPECTROSCOPIC ELLIPSOMETRY APPARATUS INCLUDING AN OPTICAL FIBER

[75] Inventors: Franck Bernoux, Paris; Jean-Louis Stehle, Colombes, both of France

[73] Assignee: Sopra-Societe De Production Et De Recherches Appliquees, Bois-Colombes, France

[21] Appl. No.: 50,766

[22] Filed: Apr. 21, 1993

Related U.S. Application Data

[63] Continuation of Ser. No. 668,394, Mar. 13, 1991, abandoned, which is a continuation of Ser. No. 22,408, Mar. 6, 1987, abandoned.

[30] Foreign Application Priority Data

Mar. 6, 1986 [FR] France .................. 86 03188

[51] Int. Cl.$^5$ .................................. G01N 21/21
[52] U.S. Cl. .................... 356/369; 356/367
[58] Field of Search ............ 356/369, 364, 365, 366, 356/367, 368; 250/225

[56] References Cited

U.S. PATENT DOCUMENTS

| | | | |
|---|---|---|---|
| H230 | 3/1987 | Smith | 356/369 |
| 4,102,574 | 7/1978 | Wieder et al. | 356/367 |
| 4,212,537 | 7/1980 | Golob et al. | 356/73.1 |
| 4,269,483 | 5/1981 | Feldtkeller | 356/368 |
| 4,439,022 | 3/1984 | Gebhardt et al. | 359/363 |
| 4,492,860 | 1/1985 | Brogardh et al. | 250/227.21 |
| 4,746,184 | 5/1988 | Gäng | 356/73.1 |
| 4,948,255 | 8/1990 | Watanabe | 356/367 |

OTHER PUBLICATIONS

LaSalle et al "A compact, concave grating, two detector, spectrum analyzer for the measurment of electron temperatures on CTR plasmas by ruby laser scattering" *Optics Communications*, vol. 17, No. 3 (Jun. 1976) pp. 325-327.

Aspnes, D. E. "Fourier Transform Detection System for Rotating-Analyzer Ellipsometers" *Optics Communications*, vol. 8, No. 3, (Jul. 1973) pp. 222-225.

Edwards et al "Automated Ellipsometer", *IBM Technical Disclosure Bulletin*, vol. 18, No. 6, (Nov. 1975) p. 2031.

Zeidler et al, "Beam Deviation Errors in Ellipsometic Measurements; an Analysis" *Applied Optics*, vol. 13, No. 8 (Aug. 1974) pp. 1938-1945.

Afanasjev et al, "The Influence of Surface Lovers on the Measured Refractive Index of Ferroelectric Materials", *Ferroelectrics*, vol. 65 (1985) pp. 175-180.

Primary Examiner—Richard A. Rosenberger
Attorney, Agent, or Firm—McAulay Fisher Nissen Goldberg & Kiel

[57] ABSTRACT

A spectroscopic ellipsometer comprises a wideband light source, together with a first optical system including a rotating polarizer which applies a parallel beam to a sample contained in an enclosure. The reflected beam is picked up by an analyzer in a second optical system which transmits said reflected beam to a monochromator which is followed by a photodetector which is connected to control electronics connected, in turn, to a microcomputer. An optical fiber is provided between the source and the first optical system. Advantageously, a second optical fiber provided between the second optical system and the monochromator.

15 Claims, 3 Drawing Sheets

SPECTROSCOPIC ELLIPSOMETRY APPARATUS INCLUDING AN OPTICAL FIBER

This is a continuation of application Ser. No. 07/668,394, filed Mar. 13, 1991 which is a continuation of Ser. No. 07/022,408 filed Mar. 6, 1987, both now abandoned.

The invention relates to ellipsometry, which can be used to make measurements concerning the surface state of a solid.

BACKGROUND OF THE INVENTION

When a light beam is reflected from a sample, its polarization is modified in a way which depends on the structure of the sample, and in particular on its reflection coefficient (rp) parallel to the plane of incidence, and on its reflection coefficient (rs) perpendicular thereto.

Two independent data items are thus obtained, namely the phase difference delta and the amplitude ratio tan psi of the parallel and perpendicular polarizations of the beam reflected from the sample. These ellipsometric parameters are defined by the equation:

$$\tan\text{psi } e^{i \cdot delta} = (rp)/(rs)$$

where e is the exponential function and i is the unit imaginary vector of complex numbers.

The optical properties of a material are defined by its real index (refractive index n) and its imaginary index (absorption coefficient k). For a thin layer of material, there is a third parameter which characterizes its optical properties: namely its thickness T. In order to characterize a multi-layer sample, three parameters are required per layer, plus the two indices of the substrate. It is then necessary to operate at a plurality of different wavelengths if information is to be obtained on all of the parameters of a multi-layer surface. Further, as the person skilled in the art is well aware, since these measurements are based on a periodic phenomenon, they suffer from ambiguity: the optical period in the layer.

Ellipsometric measurements must therefore be repeated at several different wavelengths. Initially this was done using a laser beam together with a filter for each wavelength.

More recently, spectroscopic ellipsometry has appeared in which the light emitted is taken from a wideband source and a frequency-controlled monochromator is used for separating the various different wavelengths over the entire available spectrum. Such an apparatus is described in an article entitled "Ellipsometrie Spectroscopique" by M..H. Debroux, Ged. A. Vareille, l'Echo des Recherches No. 113, 3rd quarter 1983, pages 61 to 68, and also in a notice from the (French) Centre National d'Etude des Télécommunications (CNET) entitled "Spectroscopic Ellipsometry", edition 20.2.A/CMS, dated 1st March 1984, and published by CNET's Centre Norbert Segard at Grenoble. Reference can be made to these documents for a fuller understanding of spectroscopic ellipsometry.

It also appears that spectroscopic ellipsometry is particularly advantageous for monitoring the manufacture of integrated circuits, in particular during the gas diffusion or ion implanting stages. Spectroscopic ellipsometry can also be used to accurately measure the surface state of a solid, or to investigate a phenomenon relating to such a surface, such as chemical adsorption or absorption.

Thus, a prior art spectroscopic ellipsometry apparatus comprises:

a light source;

a first optical system including a polarizer for illuminating a sample at a sloping incidence with a beam of polarized light which is collimated by a diaphragm;

a second optical system including an analyzer for picking up the light reflected by the sample; and a photodetector mounted at the outlet from said second optical system.

One of the two polarizing members constituted by the polarizer and the analyzer is subjected to continuous rotation, and in practice to rotation at a constant speed. As a result, the light received by the photodetector is amplitude modulated at a frequency equal to twice the speed of rotation of said member.

Operation is rendered monochromatic either at the light source or else at the photodetector. In spectroscopic ellipsometry, this means that a variable monochromator is located either downstream from the light source or upstream from the photodetector.

Finally, the prior apparatus also includes electronic means for control and processing purposes in order to measure the amplitude of the radiation received by the photodetector as a function of the angle of polarization so as to deduce information concerning the surface state of the sample therefrom in the manner defined above.

In theory, such apparatuses are quite simple. However, they are very difficult to produce in practice, particularly now that laser sources are no longer used and wide band light sources are used instead. Similar remarks can be made about the changeover from discrete optical filters to a monochromator capable of operating continuously over the entire spectrum used.

The main problems encountered are as follows:

Firstly, if the necessary rotation takes place at the polarizer between the light source and the object, any polarization defect in the light source will disturb the measurements. This also applies under opposite circumstances when it is the analyzer which is rotated. In this case, any sensitivity to polarization by the photodetector and in particular any dichroism in its inlet window will degrade measurements.

Secondly, the rotating member, be it the polarizer or the analyzer, produces not only a variable angle of polarization, but also a slight deflection of the beam, thereby causing the beam to follow a circular trajectory. This phenomenon can be compensated at one wavelength only and is therefore incapable of being corrected when a monochromator is used which can be adjusted over a wide optical bandwidth.

The present invention seeks to provide an improved spectroscopic ellipsometer capable of solving the above problems and also of providing other advantages.

SUMMARY OF THE INVENTION

Essentially, the invention provides a spectrometer of the type defined above in which at least one first optical fiber is disposed either between the light source and the first optical system (if that is the optical system provided with a rotating polarizer) or else between the second optical system and the photodetector (if the second optical system is provided with a rotating analyzer). In other words, the first optical fiber is mounted between the optical system which is subjected to rotating polarization and the corresponding light source or photodetector, as the case may be.

At present, it is thought that the, or each, optical fiber must be of the multimode type so as to ensure that a plurality of different optical paths exist within the fiber, thereby scrambling the polarization. This provides compensation, as the case may be, for polarization anisotropy in the light source or in the photodetector, and in particular in the inlet window to the photodetector which is often made of quartz and therefore subject to birefringence for a photon-counting photomultiplier operating over a wide band.

The geometrical characteristics of the fiber influence the polarization scrambling effect. It is presently thought that the fiber should have a length of about one meter to about ten meters. Taking account of the required mode scrambling, and also of other requirements, it is thought desirable for the diameter of the fiber to be of the order of 100 or so micrometers.

Preferably, the apparatus also includes at least one second optical fiber between the other optical system and the photodetector or the light source, as the case may be.

This solution provides several advantages which are described in greater detail below.

In practice, in a spectroscopic ellipsometer apparatus, the polarizing member which is not subjected to constant rotation is nevertheless orientable, and in particular by means of a stepper motor. Although the effects due to residual polarization are less critical in this case, an advantage can nevertheless be obtained by using a second optical fiber whenever the orientation in question is caused to vary step-by-step.

In a first type of apparatus in accordance with the invention, the light source is a wide band source and the photodetector is preceded by a monochromator which is adjustable by electronic means. In this case, the first optical fiber is mounted between the light source and the first optical system which is the optical system containing a constantly rotating polarizer. It may also be observed that when the monochromator is situated close to the detector, the first optical fiber is situated close to the source.

The second optical fiber is then placed between the second optical system and the monochromator and considerably facilitates solving the problem of the spot rotating around a circle, as mentioned above. So long as an image extending over the envelope of the circular spot motion is caused to enter the second optical fiber, and so long as all of the radiation coming from the second optical fiber is caused to enter the monochromator, this problem disappears.

In a second type of apparatus in accordance with the invention, the monochromator is placed between the wideband light source and the first optical system. The first optical fiber is placed between the second optical system which includes a rotating analyzer and the photodetector. Here again, it should be observed that when the monochromator is close to the light source, then the first optical fiber is close to the photodetector. However, a different arrangement is possible both for apparatus of the second type and for apparatus of the first type mentioned above.

In second type apparatus, the second optical fiber is naturally placed between the monochromator and the first optical system. In this case it serves to match the aperture between the outlet from the monochromator and the inlet to the first optical system and it should be observed that when the monochromator is subjected to spectrum sweeping, the direction and the starting point of its outlet beam are subjected to small displacements.

In a particular embodiment of the invention, the light source is a high-pressure xenon arc lamp; the photodetector is a photon-counting photomultiplier; and the monochromator is a two-prism type monochromator.

Apparatus of this nature normally includes means for precision displacement of the sample relative to the first and second optical systems in order to scan different points on the surface of the sample.

The use of optical fibers also provides the advantage that the light source, the monochromator, the photodetector, and the electronic means for control and processing (or at least a portion thereof) can be brought together on a single chassis at a distance from the sample.

Further, a plurality of assemblies constituted by respective samples together with pairs of optical systems may be connected by respective optical fibers in time-multiplexed manner to a common portion including said chassis, i.e. a common light source, a common monochromator, a common photodetector, and common electronic means for control and processing.

Heretofore, optical fibers have not been used within a spectroscopic electrometer, in particular because of the unavoidable signal attenuation which results therefrom, but also because of the optical constraints associated with injecting a signal into a fiber and in retrieving a signal therefrom. Account must also be taken of the complex adjustments that are required for a spectroscopic ellipsometer.

The present invention goes against established practice and makes use of at least one, and preferably two, optical fibers, in order to obtain optical advantages from the fibers which substantially compensate for the drawbacks associated with using optical fibers.

BRIEF DESCRIPTION OF THE DRAWINGS

Embodiments of the invention are described by way of example with reference to accompanying drawings, in which.

The accompanying drawings should be considered as forming an integral part of the present description and may be used, where appropriate, to add to the description and to add to the definition of the invention.

MORE DETAILED DESCRIPTION

Figure 1:
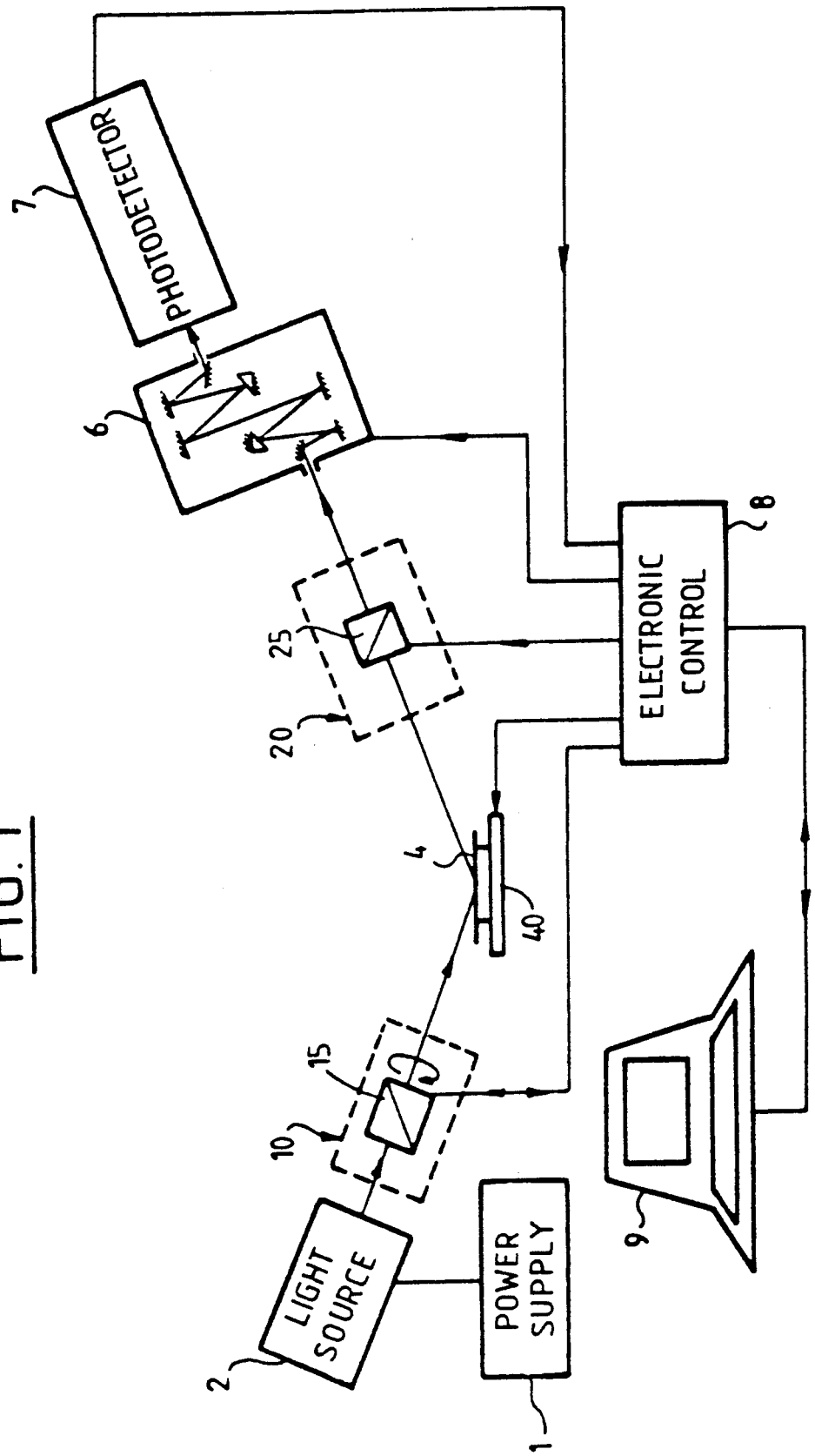
FIG. 1 is a block diagram of a prior art spectroscopic ellipsometer.

FIG. 1 is a block diagram of a prior art spectroscopic ellipsometer.

A power supply 1 excites a light source 2 such as a high-pressure xenon arc lamp. The first optical system 10 including a polarizer 15 transforms the light beam coming from the source 2 into a beam which strikes a sample 4 mounted on an object carrier 40 which is preferably movable along two orthogonal directions in a plane parallel to the plane of the object.

The useful light is the light reflected by the object symmetrically to the incident beam about a normal to the surface of the sample 4.

This reflected light is picked up by a second optical system 20, including an analyzer 25 for application to the inlet slot to a monochromator 6 which in this case is a double prism monochromator. The light coming from the outlet slot of the monochromator 6 is applied to a photodetector 7 which generally comprises a photomultiplier followed by an amplifier so as to be able to count photons over a wide band.

The equipment shown in FIG. 1 is essentially the same as the spectroscopic ellipsometer described in the above-specified CNET note. The polarizer 15 rotates at a constant speed corresponding, for example, to a frequency of 40 Hz. The analyzer 25 is orientable with an accuracy of about one hundredth of a degree under the control of a stepper motor.

Control electronics 8 acts:

on the polarizer 15 to cause it to rotate continuously;

on the object carrier 40 in order to control its X-Y positioning;

on the analyzer 25 in order to control its orientation by means of said stepper motor;

on the monochromator 6 in order to define the wavelength to which it is tuned; and finally on the signal from the photodetector 7 as applied to the control electronics 8 to record said signal in conjunction with data representative of the rotation of the polarizer 15 and with other data including, in particular, the position of the sample, the position of the analyzer, and the wavelength at which the measurement is performed.

This data may optionally be pre-processed by the control electronics 8 and is then transmitted to a microcomputer 9 suitable for deducing the above-specified tangent of psi and cosine of delta, and then for deducing curves representative of the surface state and/or the multi-layer structure of the sample as a function of each location struck by the light spot.

Inspection of FIG. 1 shows that all of the optical items from the source to the photodetector must be located in highly specific positions relative to the sample 4. In some applications it would be desirable to be able to dynamically observe phenomena taking place inside an oven. The above-specified geometrical constraint means that spectroscopic ellipsometry cannot be used for such observation. Each time an observation is made on the object, the object must be removed from the oven and placed on the object carrier, as shown in FIG. 1.

Further, and above all, the device shown in FIG. 1 is sensitive to the residual polarization of the light source constituted by the xenon arc lamp. It is also sensitive to the circular movement to which the spot on the sample 4 is subjected as the polarizer 15 rotates, and this effect is increased to some extent by the analyzer 25 since it is orientable.

The residual polarization of the light source 2 disturbs the measurement as taken by the control electronics 8. The circular movement of the spot leads to a compromise for applying the light beam to the input of the monochromator 6.

Figure 2:
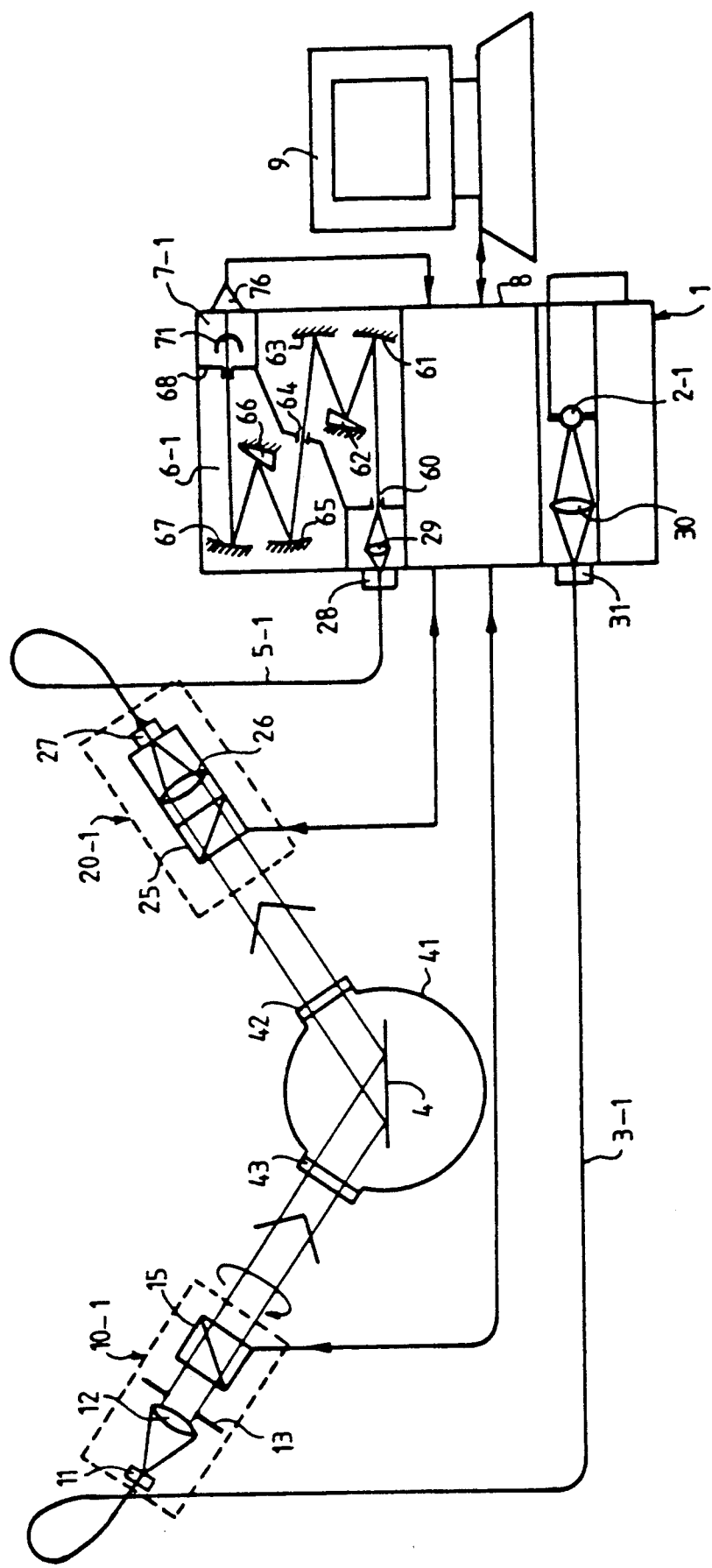
FIG. 2 is a block diagram of a first embodiment of a spectroscopic ellipsometer in accordance with the invention.

The present invention improves this situation. A first embodiment of the invention is shown in FIG. 2.

A single chassis supports the power supply 1 for the xenon lamp 2-1, the control electronics 8 which is constituted by a microprocessor, the monochromator 6-1, the photomultiplier 7-1 together with its amplifier, and optionally the microcomputer 9. Where necessary, components specific to the first embodiment of the invention are identified by a reference including the suffix "1". Where appropriate, the suffix "2" is used for the second embodiment.

The light from the source 2-1 is transmitted via a lens 30 to an inlet coupler 31 to an optical fiber 3-1.

The optical fiber is connected to the optical system 10-1 which includes an optical fiber outlet coupler 11, a lens 12, a collimator diaphragm 13, and the rotating polarizer 15.

The parallel beam from the polarizer 15 strikes an inlet window 43 made in the wall of an enclosure 41 containing the sample 4-1 (e.g. an integrated circuit being fabricated).

The reflected radiation passes through an outlet window 42 also provided in the wall of the enclosure 41 and strikes the analyzer 25 of the second optical means 20-1. A lens 26 applies the beam which passes through the polarizer 25 to the inlet coupler 27 of a second optical fiber 5-1.

The outlet from the second optical fiber 5-1 passes through an outlet coupler 28 to deliver light via a lens 29 to the inlet slot 60 of the monochromator 6-1. The monochromator comprises a first mirror 61, a first prism 62, a second mirror 63, an intermediate slot 64, a third mirror 65, a second prism 66, a fourth mirror 67, and an outlet slot 68. The outlet slot looks into the photodetector 7-1 which comprises a photomultiplier 71 and an amplifier 76. The output from the amplifier 76 is connected to the microprocessor control electronics 8 which is in turn connected to the microcomputer 9.

The presence of an enclosure 41 shows that this equipment can be used for dynamic observation of phenomena. In this respect, the optical fibers provide great flexibility since most of the sensitive elements, and in particular the heat-sensitive elements, can be kept at a distance in the above-mentioned single chassis.

The optical fiber 3-1 which may be 2 meters long, for example, has a diameter of 200 microns and is a single multimode fiber of the step-index or of the graded-index type.

It has been observed that such a fiber considerably attenuates and can even eliminate polarization defects due to the xenon lamp 2-1.

The optical fiber couplers such as 31, 11, 27 and 28 may be connectors such as those sold by the French corporation Alliance Technique Internationale (A.T.I.).

In this manner, it has been observed that considerable advantages are gained by using optical fibers in the equipment in spite of prior unfavorable prejudice against optical fibers and without the attenuation due to the fibers being excessive. The advantages obtained in terms of the signal/noise ratio are in favor of optical fibers being present compared with prior equipment.

The optical fiber 5-1 can receive all the radiation reflected from the sample 4-1, taking account of the rotation to which the spot is subjected under the effect of polarizer rotation, and of further deflection provided by the analyzer. This can be done by focussing the radiation as a whole on the inlet coupler 27 to the optical fiber so that the entire zone affected by these rotation phenomena conveys its light radiation into the optical fiber 5-1. At the other end, the coupler 28 and the associated lens 29 then make it possible to ensure that the major portion of the useful radiation is injected into the monochromator 6-1 via its inlet slot 60 and along a fixed direction. As a result of this, the attenuation due to using a relatively long optical fiber can be substantially compensated by the increase in the level of the useful signal which results from using equipment in accordance with the invention.

The exploitation of the signals by the microprocessor control electronics 8 and by the microcomputer 9 may take place in conventional manner, although it should be observed that it is now possible to dynamically follow an on-going phenomenon.

In some applications, the FIG. 1 disposition may need to be connected the other way around, i.e. the polarizer 15 should be orientable using a stepper motor while the analyzer 25 should be rotated continuously.

Similarly, in some cases, it may be advantageous to place the monochromator 6-1 between the source and the optical fiber 3-1 rather than between the optical fiber 5-1 and the photodetector 7-1.

This is particularly true for applications which perform X-Y mapping of a sample which can now be scanned statically. The following description with reference to FIG. 3 of a second embodiment of the invention is particularly suitable for such an application.

Figure 3:
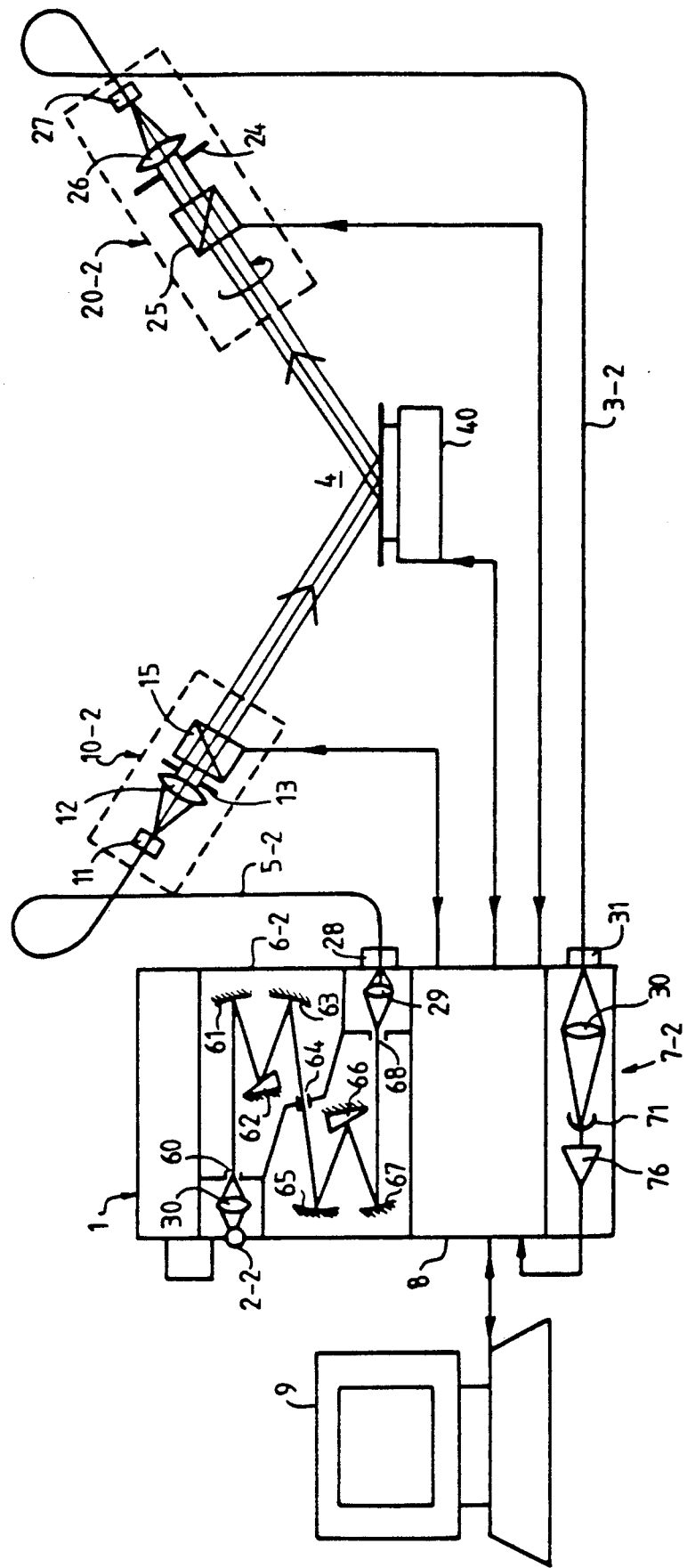
FIG. 3 is a block diagram of a second embodiment of a spectroscopic ellipsometer in accordance with the invention.

In order to facilitate understanding, it is preferable to leave the optical path of the light rays unchanged, which has the effect, given the above-mentioned symmetry between the equipments shown in FIGS. 2 and 3, of putting the chassis and the microcomputer 9 to the left in FIG. 3.

As before, the chassis includes a power supply 1 for the xenon source 2-2, the monochromator 6-2, the microprocessor control electronics 8, and the photodetector 7-2.

As in FIG. 1, the sample 4 is placed on an object carrier 40 which can be moved in X and in Y directions in a plane parallel to the surface of the sample.

More precisely, the radiation emitted by the source 2-2 is picked up by a lens 30 which applies it to the inlet slot of the monochromator 6-2. Otherwise, the monochromator 6-2 is identical to the monochromator 6-1.

The outlet slot 68 from the monochromator 6-2 illuminates a lens 29 which makes an image thereof on the inlet coupler 28 to the second optical fiber 5-2.

The constraints on the length, the diameter, and the constitution of the optical fibers are the same as above.

The outlet from the optical fiber 5-2 passes via a coupler 11 and a lens 12 into the first optical system 10-2. The lens 12 is followed by a diaphragm 13 which collimates the beam prior to the beam striking the polarizer 15 which is orientable under the control of a stepper motor.

The beam reflected from the sample strikes the analyzer 25 of the second optical system. This analyzer is followed by a diaphragm 24 and then by a lens 28 whose outlet beam strikes the inlet coupler 27 to the first optical fiber 3-2.

The outlet coupler 31 from said first optical fiber 3-2 is placed looking into a lens 30 which forms an image thereof on the inlet window to the detector. More precisely, this inlet window is the inlet to a photomultiplier 71 which feeds an amplifier 76 which is connected, in turn, to the microprocessor control electronics 8.

The first optical fiber 3-2 connected to the rotating analyzer 27 has the effect of attenuating or completely eliminating the unwanted consequences on the measurements due to any polarization defect which may occur in the quartz inlet window to the photomultiplier 71.

The second optical fiber 5-2 adapts without difficulty to small variations in the position or the direction of the outlet beam coming through the slot 68 of the monochromator 6-2. This is achieved so long as the beam strikes coupler 28 properly, in which case it is certain that the incident beam (which is monochromatic in this embodiment) is indeed completely received by the first optical system 10-2 and is therefore used fully and in fixed direction for reflection on the sample.

As above, advantages are thus gained from using optical fibers instead of the drawbacks which could have been expected due to the attenuation of the optical fibers and their inlet and outlet couplers.

In general, when using calcite polarizers together with other components of the type specified above, it is possible to operate over a spectrum running from about 230 nanometers to about 930 nanometers, and this band may be extended up to about 3 micrometers provided the photomultiplier is replaced by some other form of detector suitable for operating in the infrared since no photon-counting photomultipliers currently exist suitable for operating at more than 1.1 micrometers.

As mentioned above, it is presently considered desirable for the optical fiber to be at least 1 meter long, to be preferably about 2 meters long, and it may be as much as 10 meters or more long.

The diameter of the optical fiber is preferably about 200 microns, at least providing the monochromator has an aperture of about F/8 while the fiber has an aperture of F/2. The intermediate optics then needs to have a magnification of 4. A 200-micron diameter fiber thus produces a spot having a diameter of 800 microns and the major portion thereof can enter the inlet slot of the monochromator.

At the other end, a fiber diameter of 200 microns has proved suitable for receiving the entire useful signal into the fiber, even when account is taken of the movement of the spot due to polarization rotation.

If work is to be performed in the ultraviolet, the length of the fiber should be close to the lower limit as defined above.

The improved accuracy which can be obtained by using apparatus in accordance with the invention is important not only for its own sake. Subsequent exploitation of the spectroscopic ellipsometry signals makes use of a modelling technique, i.e. a model curve is established which corresponds to the estimated structure of the sample surface and an attempt is made to correlate said model curve with the real measurement points obtained over the entire spectrum. The person skilled in the art knows that in such cases, the quality of the model depends to a very large extent on the reliability of the measurement signals obtained.

Further, the invention also makes another technique of spectroscopic ellipsometry measurement more easy, and this consists in performing "tracking". In this technique, instead of leaving the analyzer or the orientable polarizer in fixed positions through an entire series of measurements, the analyzer or polarizer in question is displaced for each wavelength so as to occupy optimum conditions for measurement. This technique is very difficult to implement using prior art devices.

In the FIG. 3 embodiment, various points on the surface of the object can be analyzed by displacing the object carrier 40. In the embodiment shown in FIG. 2, an equivalent effect can be obtained by displacing the optical systems 10-1 and 20-1. It may be observed that such displacement, which is made possible by the use of optical fibers, is not possible with prior art equipment of the kind shown in FIG. 1, nor is it possible to vary the angle of incidence with such equipment.

Once most of the essential and more expensive components of the spectroscopic ellipsometry apparatus are mounted together on a common chassis, it becomes possible to use these items, together with the microprocessor 9, in common for a plurality of measuring assemblies each of which comprises a sample and a sample carrier, or else a sample in an oven, together with an associated pair of optical systems 10 and 20 and the associated optical fibers 3 and 5.

This can be done by providing multiple electrical connections with control signals being time multiplexed, and by causing the optical fibers to co-operate in multiplexed manner with the source 2, and finally by putting the optical fibers side-by-side in front of the inlet slot 60 to the monochromator whose long length is particularly suitable for such a setup. The above-specified details are suitable, in particular, for the equipment shown in FIG. 2, but it will readily be appreciated that a similar arrangement is possible with the FIG. 3 embodiment.

Finally, it is repeated that the equipments shown in FIGS. 2 and 3 are substantially symmetrical, optically. Equipment can therefore be constructed capable of operating simultaneously or in multiplexed mode both as a FIG. 2 embodiment and as a FIG. 3 embodiment of the invention.

Naturally, the present invention is not limited to the embodiments described herein. It covers any variant thereof falling within the scope of the accompanying claims.

We claim:

1. Spectroscopic ellipsometry apparatus, comprising a light source;
a first optical system including a polarizer for illuminating a sample with a beam of polarized light at a sloping incidence;
a second optical system including an analyzer for picking up the light reflected from the sample, said second optical system having an outlet;
a photodetector mounted at said outlet of said second optical system;
one of the two polarizing members constituted by the polarizer and by the analyzer being subjected to rotation at a known speed;
means for permitting spectrum selection of the incident light or for permitting spectrum analysis of the reflected light; and
control and processing electronic means for measuring the amplitude of the radiation received by the photodetector as a function of the angle of polarization in order to deduce information concerning the surface state of the sample;
said apparatus including the improvement of one first multimode optical fiber disposed between the optical system subjected to rotating polarization and its associated light source or photodetector as the case may be and a second optical fiber between the other optical system and its associated photodetector or light source as the case may be.

2. Spectroscopic ellipsometry apparatus, comprising:
a wide-band light source having a polarization anisotropy;
a first optical system including a polarizer for illuminating a sample with a beam of polarized light at a sloping incidence;
a second optical system including an analyzer for picking up the light reflected from the sample, said second optical system having an outlet;
a photodetector mounted at said outlet of said second optical system;
one of the two polarizing members constituted by the polarizer and by the analyzer being subjected to rotation at a known speed;
means for permitting spectrum selection of the incident light or for permitting spectrum analysis of the reflected light; and
control and processing electronic means for measuring the amplitude of the radiation received by the photodetector as a function of the angle of polarization in order to deduce information concerning the surface state of the sample;
said apparatus including the improvement of at least one first multimode optical fiber having a length sufficient for providing light depolarization disposed between the optical system subjected to rotating polarization and its associated light source or photodetector as the case may be:
said first optical fiber having an entrance with a size and shape to substantially eliminate effects of any deflection of a light beam caused by said rotating member when disposed between the optical system subjected to rotating polarization and the photodetector;
said photodetector being preceded by a monochromator which is adjustable by electronic means; said first optical fiber being mounted between said light source and said first optical system including the rotating polarizer member; and
wherein a second optical fiber is placed between the second optical system and said monochromator.

3. Spectroscopic ellipsometry apparatus, comprising:
a wide-band light source having a polarization anisotropy;
a first optical system including a polarizer for illuminating a sample with a beam of polarized light at a sloping incidence;
a second optical system including an analyzer for picking up the light reflected from the sample, said second optical system having an outlet;
a photodetector mounted at said outlet of said second optical system;
one of the two polarizing members constituted by the polarizer and by the analyzer being subjected to rotation at a known speed;
means for permitting spectrum selection of the incident light or for permitting spectrum analysis of the reflected light; and
control and processing electronic means for measuring the amplitude of the radiation received by the photodetector as a function of the angle of polarization in order to deduce information concerning the surface state of the sample;
said apparatus including the improvement of at least one first multimode optical fiber having a length sufficient for providing light depolarization disposed between the optical system subjected to rotating polarization and its associated light source or photodetector as the case may be;
said first optical fiber having an entrance with a size and shape to substantially eliminate effects of any deflection of a light beam caused by said rotating member when disposed between the optical system subjected to rotating polarization and the photodetector;
a monochromator being disposed between said light source and the first optical system; said first optical fiber being placed between the second optical system including the rotating analyzer member and the photodetector; and wherein a second optical fiber is placed between the monochromator and the first optical system.

4. Spectroscopic ellipsometry apparatus, comprising:

a wide-band light source having a polarization anisotropy;

a first optical system including a polarizer for illuminating a sample with a beam of polarized light at a sloping incidence;

a second optical system including an analyzer for picking up the light reflected from the sample, said second optical system having an outlet;

a photodetector mounted at said outlet of said second optical system;

one of the two polarizing members constituted by the polarizer and by the analyzer being subjected to rotation at a known speed;

means for permitting spectrum selection of the incident light or for permitting spectrum analysis of the reflected light; and control and processing electronic means for measuring the amplitude of the radiation received by the photodetector as a function of the angle of polarization in order to deduce information concerning the surface state of the sample;

said apparatus including the improvement of at least one first multimode optical fiber having a length sufficient for providing light depolarization disposed between the optical system subjected to rotating polarization and its associated light source or photodetector as the case may be;

said first optical fiber having an entrance with a size and shape to substantially eliminate effects of any deflection of a light beam caused by said rotating member when disposed between the optical system subjected to rotating polarization and the photodetector, said apparatus having a second optical fiber between the other optical system and its associated photodetector or light source as the case may be.

5. Apparatus according to claim 4, wherein each optical fiber has a diameter of about 100 micrometers and a length of 1 meter to 10 meters.

6. Apparatus according to claim 4, wherein that one of said polarizing members which is not subjected to said rotation is itself orientable, in particular by means of a stepper motor.

7. Apparatus according to claim 4, wherein the photodetector is preceded by a monochromator which is adjustable by electronic means, and wherein the first optical fiber is mounted between the light source and the first optical system including the rotating polarizer.

8. Apparatus according to claim 4, wherein a monochromator is placed between the light source and the first optical system, and wherein the first optical fiber is placed between the second optical system including the rotating analyzer member, and the photodetector.

9. Apparatus according to claim 4, wherein the light source is a xenon arc lamp, and wherein the photodetector is a photoncounting photomultiplier.

10. Apparatus according to claim 4, including a two-prism monochromator.

11. Apparatus according to claim 4, including means for accurately displacing the sample relative to said first and second optical systems.

12. Apparatus according to claim 4, wherein the light source, the photodetector, the control and processing electronic means, together with the monochromator, if any, are all located on a common chassis.

13. Apparatus according to claim 4, wherein a plurality of assemblies comprising respective samples and pairs of optical systems are connected in time multiplexed manner by optical fibers to a common portion including the light source, the monochromator, if any, the photodetector, and the control and processing electronic means.

14. Apparatus according to claim 4, further comprising collimating means between said optical fiber and said optical system subject to rotating polarization.

15. Apparatus according to claim 4 wherein said photodetector has an inlet window having birefringence effect.

* * * * *